(12) United States Patent
Jeong et al.

(10) Patent No.: US 10,301,654 B2
(45) Date of Patent: May 28, 2019

(54) METHOD OF PREPARING CINNAMALDEHYDE

(71) Applicant: INTELLIGENT SYNTHETIC BIOLOGY CENTER, Daejeon (KR)

(72) Inventors: Ki Jun Jeong, Daejeon (KR); Sun Chang Kim, Daejeon (KR); Hyun Bae Bang, Daejeon (KR); Yoon Hyeok Lee, Daejeon (KR); Suk Chae Jung, Daejeon (KR)

(73) Assignee: INTELLIGENT SYNTHETIC BIOLOGY CENTER, Daejeon (KR)

( * ) Notice: Subject to any disclaimer, the term of this patent is extended or adjusted under 35 U.S.C. 154(b) by 0 days.

(21) Appl. No.: 15/511,634

(22) PCT Filed: May 13, 2016

(86) PCT No.: PCT/KR2016/005085
§ 371 (c)(1),
(2) Date: Mar. 15, 2017

(87) PCT Pub. No.: WO2016/182386
PCT Pub. Date: Nov. 17, 2016

(65) Prior Publication Data
US 2018/0105844 A1    Apr. 19, 2018

(30) Foreign Application Priority Data

May 14, 2015 (KR) .......................... 10-2015-0067557

(51) Int. Cl.
| | | |
|---|---|---|
| *C12P 7/24* | (2006.01) |
| *C12N 9/00* | (2006.01) |
| *C12N 9/06* | (2006.01) |
| *C12N 9/88* | (2006.01) |
| *C12N 15/00* | (2006.01) |
| *C12N 1/20* | (2006.01) |
| *C07H 21/04* | (2006.01) |
| *C12N 15/63* | (2006.01) |

(Continued)

(52) U.S. Cl.
CPC .................. *C12P 7/24* (2013.01); *C12N 9/00* (2013.01); *C12N 9/0008* (2013.01); *C12N 9/88* (2013.01); *C12N 9/93* (2013.01); *C12N 15/63* (2013.01); *C12N 15/70* (2013.01); *C12Y 102/01044* (2013.01); *C12Y 403/01024* (2013.01); *C12Y 602/01012* (2013.01)

(58) Field of Classification Search
None
See application file for complete search history.

(56) References Cited

U.S. PATENT DOCUMENTS 8,975,063 B2* 3/2015 Smolke .................. C12P 17/12
435/122

FOREIGN PATENT DOCUMENTS

| CN | 104498540 | 4/2015 |
| JP | 4-211369 | 7/2004 |

(Continued)

OTHER PUBLICATIONS

GenBank Accession No. AAF81735.1, dated Jul. 1, 2002.
(Continued)

*Primary Examiner* — Yong D Pak
(74) *Attorney, Agent, or Firm* — Parker Highlander PLLC

(57) ABSTRACT

Provided is a method of preparing cinnamaldehyde by using a recombinant microorganism.

10 Claims, 7 Drawing Sheets
Specification includes a Sequence Listing.

(51) Int. Cl.
C12N 15/70 (2006.01)
C12N 9/02 (2006.01)

(56) References Cited

FOREIGN PATENT DOCUMENTS

| JP | 11-501295 | | 1/2011 | |
|---|---|---|---|---|
| JP | 2011-223981 A | | 11/2011 | |
| KR | 10-2003-0033282 | | 6/2003 | |
| KR | 10-0624236 | | 4/2005 | |
| KR | 10-0683113 | | 2/2007 | |
| KR | 10-2013-0038000 | | 4/2013 | |
| KR | 2014142648 | * | 12/2014 | |
| WO | WO 97-35471 A2 | | 10/1997 | |
| WO | WO 02-50294 A1 | | 6/2002 | |
| WO | WO-2012103555 A2 | * | 8/2012 | ......... C12N 15/8217 |
| WO | WO-2012122333 A1 | * | 9/2012 | ........... C12N 9/0071 |

OTHER PUBLICATIONS

GenBank Accession No. AF254925.1, dated Jul. 1, 2002.
GenBank Accession No. AL939119.1, dated Feb. 6, 2015.
Hsu et al. "A genetic marker of 4-coumarate: coenzyme A ligase gene in the cinnamaldehyde-chemotype Cinnamomum osmophloeum." (2012): 897-904.
NCBI Reference Sequence NM__101463.3, dated Jan. 22, 2014.
NCBI Reference Sequence NP_173047.1, dated Jan. 22, 2014.
NCBI Reference Sequence WP_011029620.1, dated Jul. 18, 2013.
Bang, Hyun Bae, et al. "Metabolic engineering of *Escherichia coli* for the production of cinnamaldehyde." *Microbial cell factories* 15.1 (2016): 16.
Extended European search report issued in European patent application No. 16793032.0, dated Jan. 9, 2018.
Kaneko, Masafumi, Yasuo Ohnishi, and Sueharu Horinouchi. "Cinnamate: coenzyme A ligase from the filamentous bacterium Streptomyces coelicolor A3 (2)." *Journal of bacteriology* 185.1 (2003): 20-27.
Lauvergeat, Virginie, et al. "Two cinnamoyl-CoA reductase (CCR) genes from *Arabidopsis thaliana* are differentially expressed during development and in response to infection with pathogenic bacteria." *Phytochemistry* 57.7 (2001): 1187-1195.
Noda, Shuhei, et al. "Benzoic acid fermentaton from starch and cellulose via a plant-like β-oxidation pathway in Streptomyces maritimus." *Microbial cell factories* 11.1 (2012): 49.

* cited by examiner

[FIG. 1]
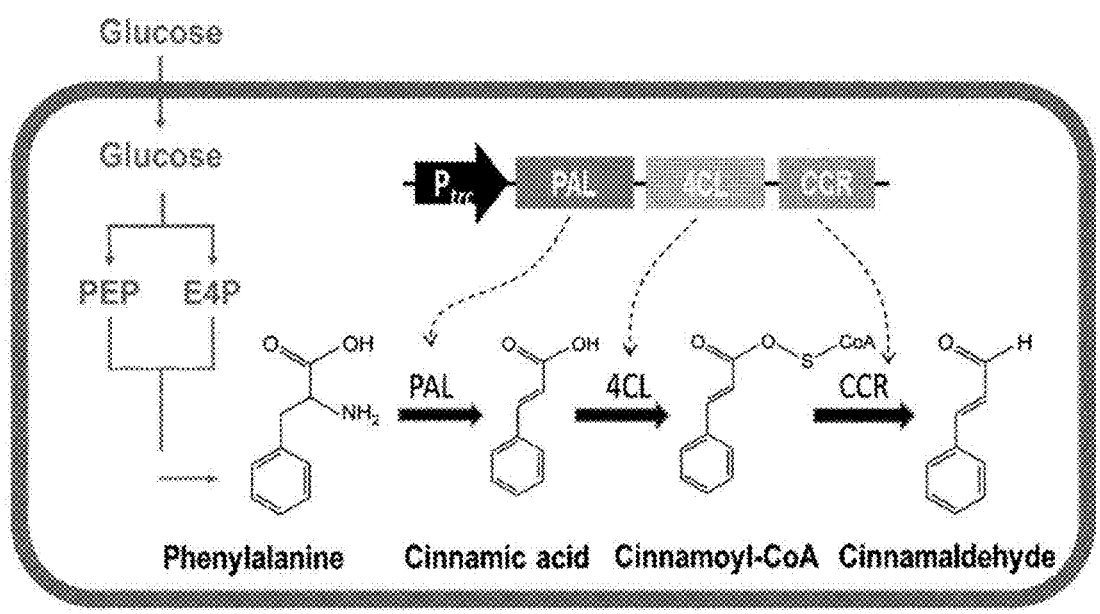

[FIG. 2]
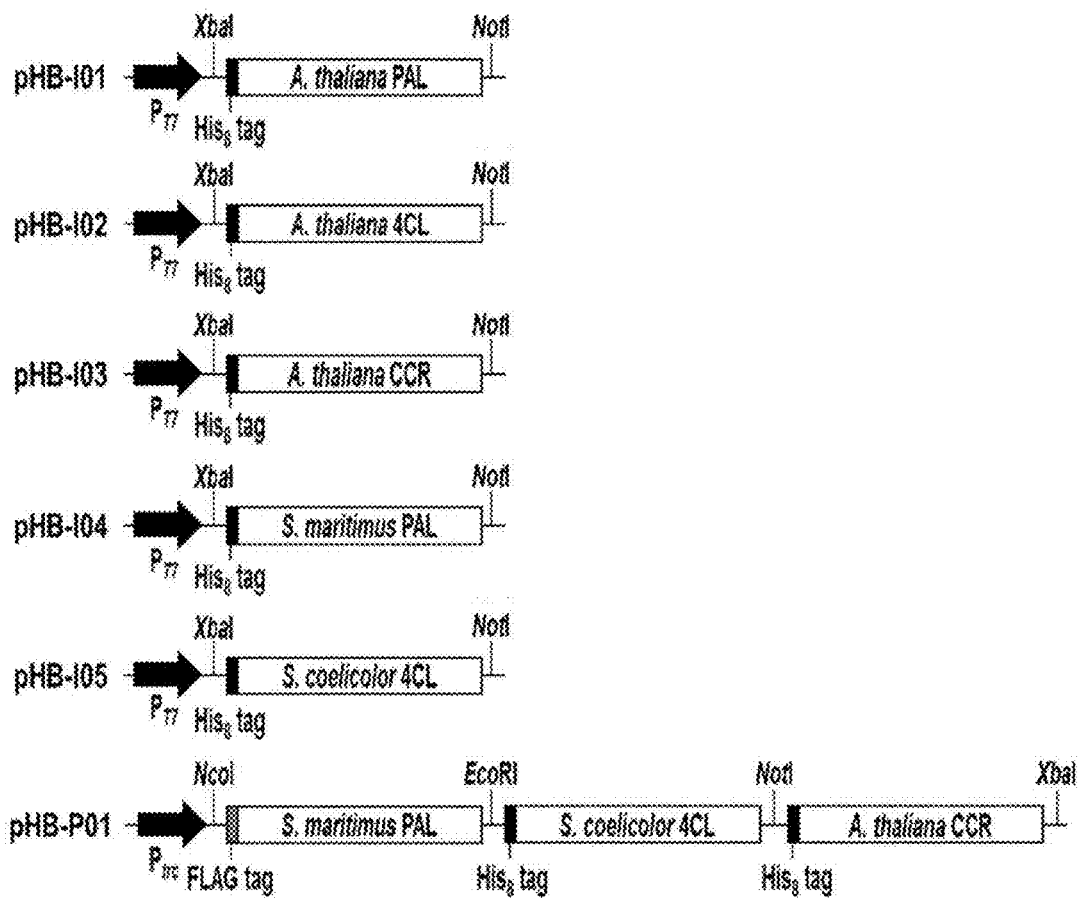
[FIG. 3]
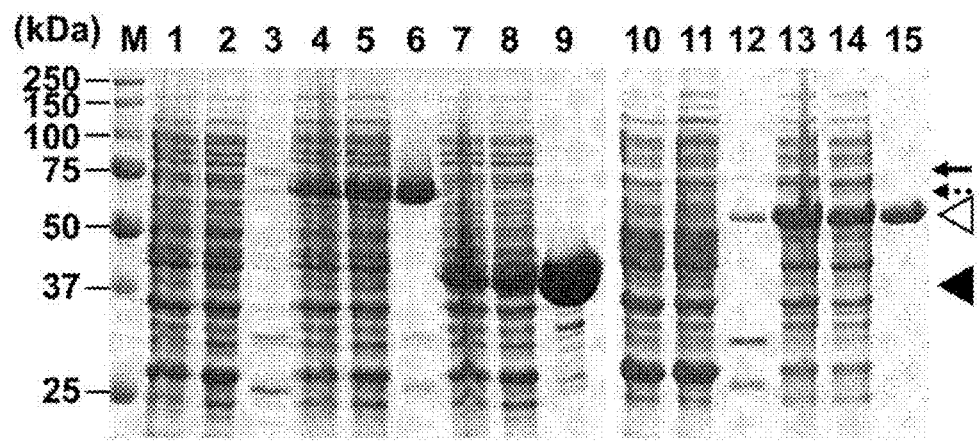

[FIG. 4]
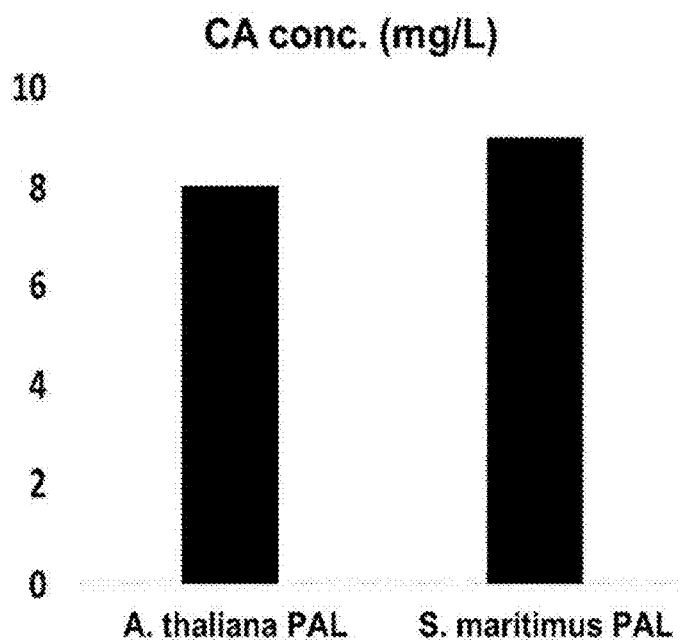
[FIG. 5]
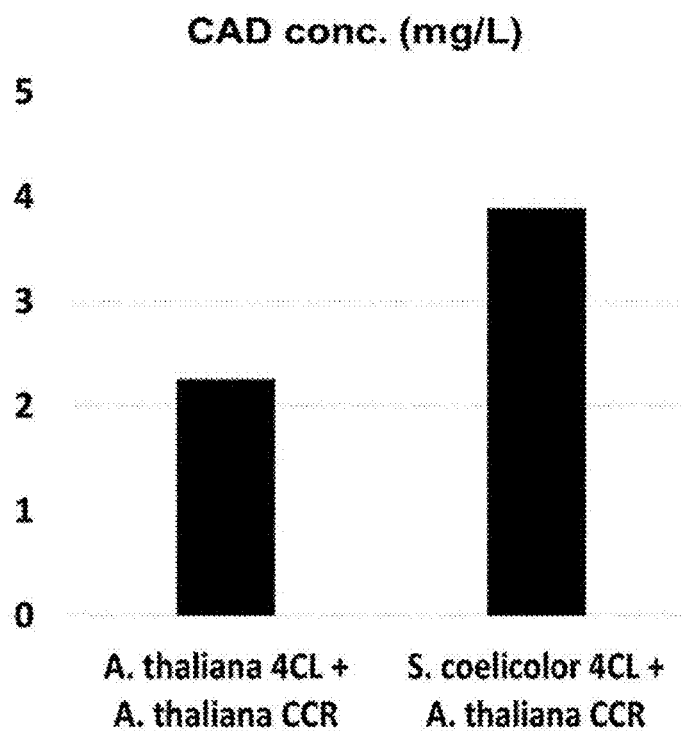

[FIG. 6]
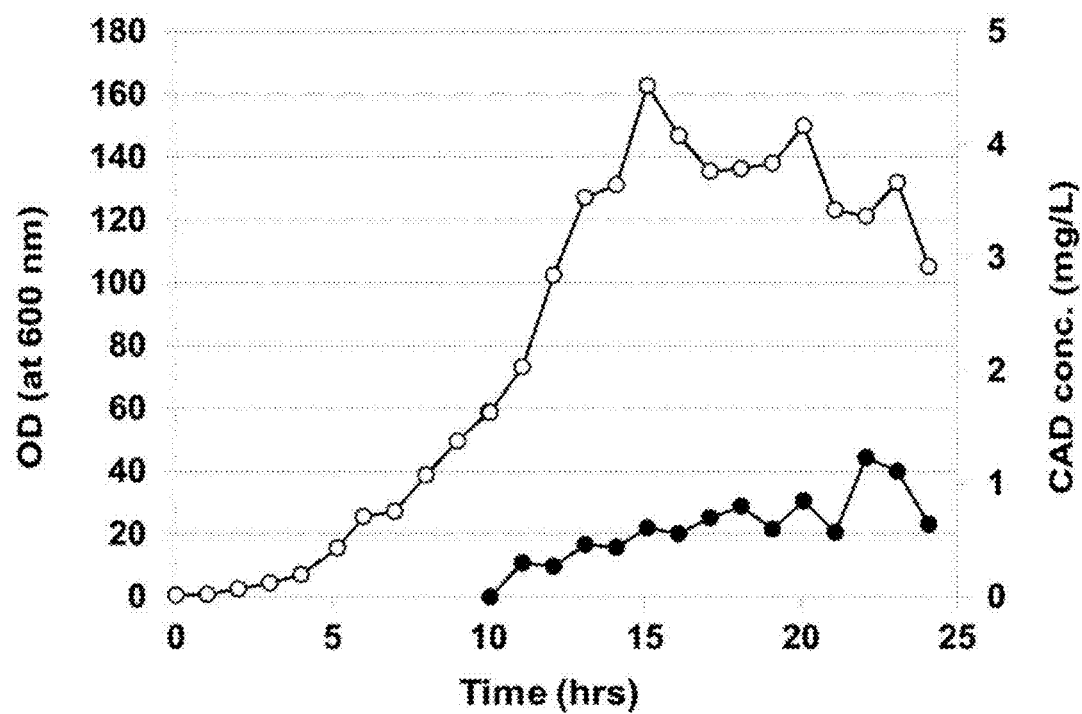

[FIG. 7]
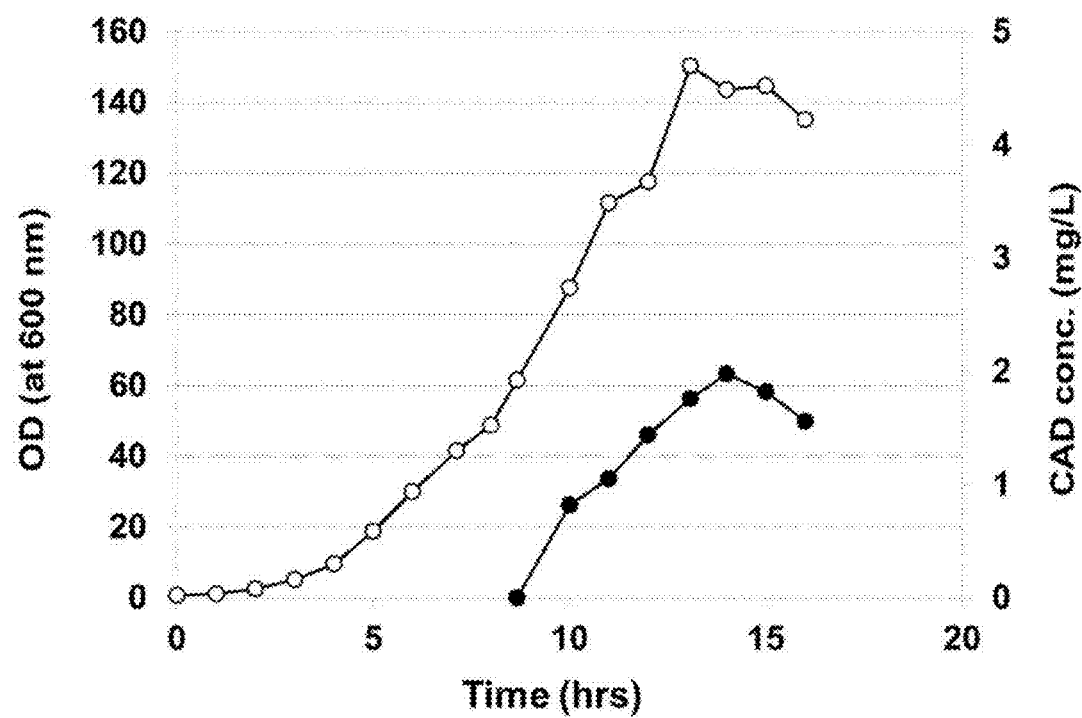

[FIG. 8]
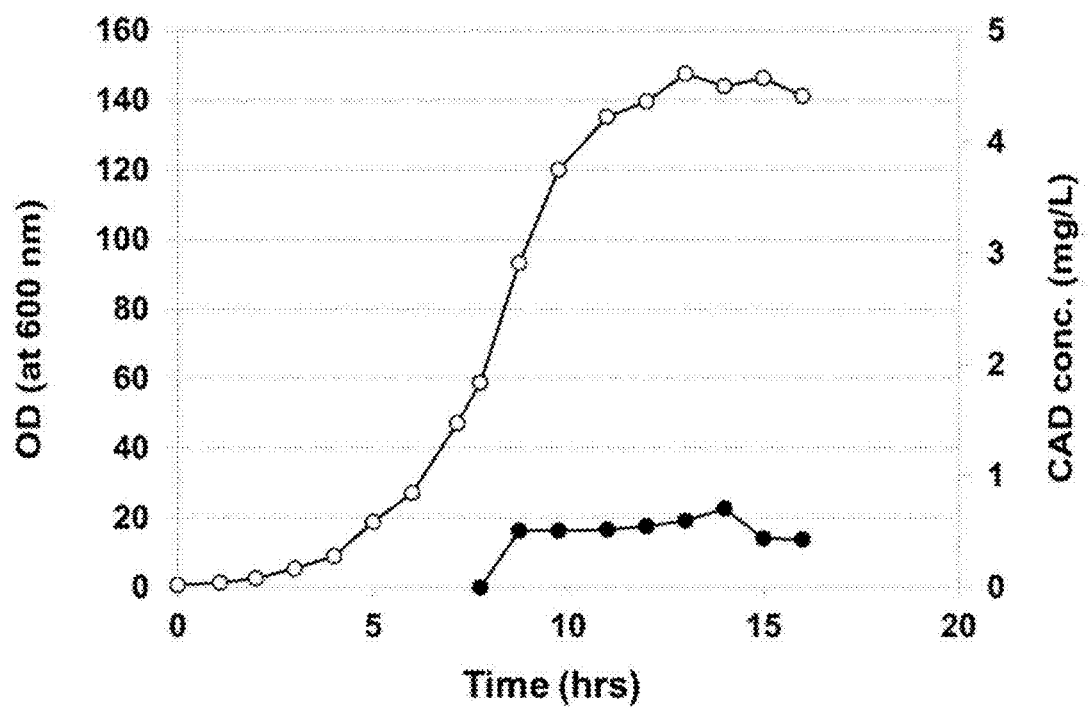

[FIG. 9]
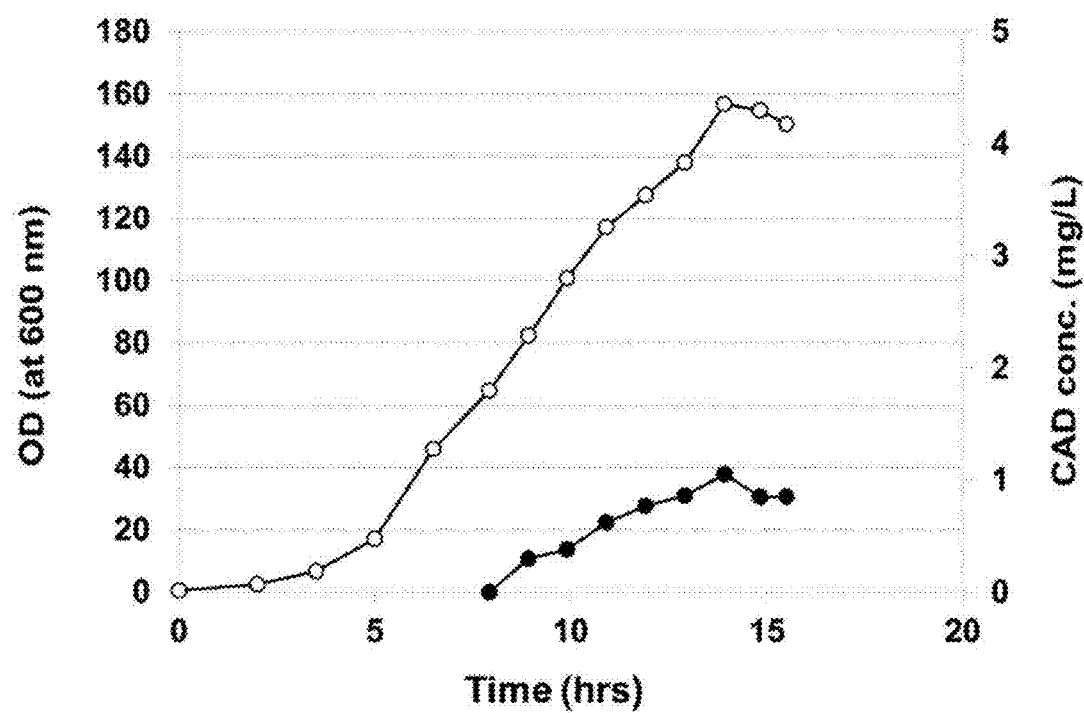

METHOD OF PREPARING CINNAMALDEHYDE

This application is a national phase application under 35 U.S.C. § 371 of International Application No. PCT/KR2016/005085, filed May 13, 2016, which claims priority to Korean Application No. 10-2015-0067557, filed May 14, 2015, which are incorporated herein in their entirety.

BACKGROUND OF THE INVENTION

1. Field of the Invention

The present invention relates to a method of preparing cinnamaldehyde by using a recombinant microorganism.

2. Description of the Related Art

Cinnamaldehyde is the primary compound responsible for cinnamon flavor and odor, and accounts for 90% of cinnamon essential oil. Cinnamaldehyde is mainly prepared by adding a concentrated sodium bisulfite solution to cinnamon oil or *cassia* oil, separating a produced additive and washing it with ethanol, degrading a resulting product in dilute sulfuric acid or sodium carbonate aqueous solution, followed by steam distillation and vacuum distillation. Alternatively, cinnamaldehyde is prepared by adding acetaldehyde dropwise to a mixture of benzaldehyde, water, and sodium hydroxide under stirring, extracting a reaction product with benzene, followed by fractional distillation under reduced pressure.

Cinnamaldehyde is used in a variety of applications. For example, Korean Patent Publication No. 2003-0033282 describes antioxidant activity of cinnamaldehyde, and Korean Patent No. 10-0683113 describes a therapeutic effect of cinnamaldehyde on obesity. Korean Patent Publication No. 2013-0038000 describes a therapeutic effect of trans-cinnamaldehyde separated from cinnamon on hepatitis B.

It is necessary to study a method of effectively producing cinnamaldehyde which is known to have such various useful effects. Korean Patent No. 10-0624236 describes a method of preparing a cinnamaldehyde derivative by heating and refluxing a benzaldehyde derivative and vinyl acetate in an acetonitrile solvent in the presence of potassium carbonate and water.

Under this background, the present inventors have made many efforts to develop a method of efficiently producing cinnamaldehyde. As a result, they found that cinnamaldehyde may be prepared in a high yield by using a recombinant strain including a pal gene derived from *Streptomyces maritimus*, a 4cl gene derived from *Streptomyces coelicolor*, and a ccr gene derived from *Arabidopsis thaliana*, thereby completing the present invention.

SUMMARY OF THE INVENTION

An object of the present invention is to provide an expression cassette for producing cinnamaldehyde, including a pal (phenylalanine ammonia lyase) gene derived from *Streptomyces maritimus*, a 4cl (4-coumarate:CoA ligase) gene derived from *Streptomyces coelicolor*, and a ccr (cinnamoyl Co-A reductase) gene derived from *Arabidopsis thaliana*.

Another object of the present invention is to provide a vector for producing cinnamaldehyde, including the expression cassette.

Still another object of the present invention is to provide a transformant for producing cinnamaldehyde, including the vector.

Still another object of the present invention is to provide a method of preparing cinnamaldehyde, including culturing the strain.

BRIEF DESCRIPTION OF THE DRAWINGS

FIG. 1 is a diagram showing a cinnamaldehyde production system according to an exemplary embodiment of the present invention.

FIG. 2 shows respective plasmids which were constructed for expression of PAL, 4CL, and CCR used in an exemplary embodiment of the present invention.

FIG. 3 is SDS-PAGE showing quantities of purified PAL, 4CL, and CCR proteins.

FIGS. 4 and 5 show concentrations of final products, cinnamate (CA) and cinnamaldehyde (CAD), respectively.

FIG. 6 shows optical density ($OD_{600}$; open circle) measured at each time point and a concentration of cinnamaldehyde (CAD con.; closed circle), after a transformant was cultured in complex medium 1.

FIG. 7 shows optical density ($OD_{600}$; open circle) measured at each time point and a concentration of cinnamaldehyde (CAD con.; closed circle), after the transformant was cultured in complex medium 2.

FIG. 8 shows optical density ($OD_{600}$; open circle) measured at each time point and a concentration of cinnamaldehyde (CAD con.; closed circle), after the transformant was cultured in defined medium 1.

FIG. 9 shows optical density ($OD_{600}$; open circle) measured at each time point and a concentration of cinnamaldehyde (CAD con.; closed circle), after the transformant was cultured in defined medium 2.

DETAILED DESCRIPTION OF THE PREFERRED EMBODIMENTS

In an aspect to achieve the above objects, the present invention provides an expression cassette for producing cinnamaldehyde including cinnamaldehyde biosynthesis genes, a vector including the same, a transformant including the same, or a method of preparing cinnamaldehyde by using the same.

The present inventors prepared a microorganism introduced with cinnamaldehyde biosynthesis genes, a pal (phenylalanine ammonia lyase) gene, a 4cl (4-coumarate:CoA ligase) gene, and a ccr (cinnamoyl Co-A reductase) gene, and as a result, they found that cinnamaldehyde may be produced from the microorganism in a yield of 1.98 mg/L (FIGS. 6 to 9).

Further, they found that a combination of PAL derived from *Streptomyces maritimus*, 4CL derived from *Streptomyces coelicolor*, and CCR derived from *Arabidopsis thaliana* shows a superior activity, compared to genes derived from other microorganisms (FIGS. 4 and 5).

Hereinafter, an expression cassette for producing cinnamaldehyde of the present invention will be described in detail.

The "cinnamaldehyde biosynthesis genes", as used herein, refer to a pal (phenylalanine ammonia lyase) gene, a 4cl (4-coumarate:CoA ligase) gene, and a ccr (cinnamoyl Co-A reductase) gene.

The pal gene may be derived from *Streptomyces maritimus*. In an embodiment of the present invention, it was confirmed that PAL enzyme derived from *Streptomyces mar-*

*itimus* has a superior enzymatic activity to PAL enzyme derived from *Arabidopsis thaliana* (FIG. 4).

For non-limiting example, the pal gene may include a nucleotide sequence represented by SEQ ID NO: 1 or SEQ ID NO: 19. The pal gene may be represented by a sequence having 70% or higher, preferably 80% or higher, more preferably 90% or higher, or much more preferably 95% sequence homology to the nucleotide sequence represented by SEQ ID NO: 1 or SEQ ID NO: 19. It is apparent that the pal gene may also include a sequence modified by substitution, deletion, insertion, or a combination thereof one or more nucleotides in the above sequence.

For non-limiting example, the pal gene may encode a PAL protein having an amino acid sequence represented by SEQ ID NO: 2. The PAL protein may include all peptides, in which various amino acid sequences are added to N- or C-terminus of the amino acid sequence of SEQ ID NO: 2, as long as the protein has phenylalanine ammonia lyase activity. In addition, the PAL protein means a peptide further including a targeting sequence, tag, labeled residue, and an amino acid sequence designed for the specific purpose of increasing a half-life or stability of the peptide at the N- or C-terminus of the peptide represented by SEQ ID NO: 2. Furthermore, the PAL protein means a protein variant, in which part of amino acids in the amino acid sequence of SEQ ID NO: 2 is modified by a method such as addition, substitution, deletion, etc.

The 4cl gene may be derived from *Streptomyces coelicolor*.

For non-limiting example, the 4cl gene may include a nucleotide sequence represented by SEQ ID NO: 3. The 4cl gene may be represented by a sequence having 70% or higher, preferably 80% or higher, more preferably 90% or higher, or much more preferably 95% sequence homology to the nucleotide sequence represented by SEQ ID NO: 3. It is apparent that the 4cl gene may also include a sequence modified by substitution, deletion, insertion, or a combination thereof one or more nucleotides in the above sequence.

For non-limiting example, the 4cl gene may encode a 4CL protein having an amino acid sequence represented by SEQ ID NO: 4. The 4CL protein may include all peptides, in which various amino acid sequences are added to N- or C-terminus of the amino acid sequence of SEQ ID NO: 4, as long as the protein has 4-coumarate:CoA ligase activity. In addition, the 4CL protein means a peptide further including a targeting sequence, tag, labeled residue, and an amino acid sequence designed for the specific purpose of increasing a half-life or stability of the peptide at the N- or C-terminus of the peptide represented by SEQ ID NO: 4. Furthermore, the 4CL protein means a protein variant, in which part of amino acids in the amino acid sequence of SEQ ID NO: 4 is modified by a method such as addition, substitution, deletion, etc.

The ccr gene may be derived from *Arabidopsis thaliana*.

For non-limiting example, the ccr gene may include a nucleotide sequence represented by SEQ ID NO: 5. The ccr gene may be represented by a sequence having 70% or higher, preferably 80% or higher, more preferably 90% or higher, or much more preferably 95% sequence homology to the nucleotide sequence represented by SEQ ID NO: 5. It is apparent that the ccr gene may also include a sequence modified by substitution, deletion, insertion, or a combination thereof one or more nucleotides in the above sequence.

For non-limiting example, the ccr gene may encode a CCR protein having an amino acid sequence represented by SEQ ID NO: 6. The CCR protein may include all peptides, in which various amino acid sequences are added to N- or C-terminus of the amino acid sequence of SEQ ID NO: 6, as long as the protein has cinnamoyl Co-A reductase activity. In addition, the CCR protein means a peptide further including a targeting sequence, tag, labeled residue, and an amino acid sequence designed for the specific purpose of increasing a half-life or stability of the peptide at the N- or C-terminus of the peptide represented by SEQ ID NO: 6. Furthermore, the CCR protein means a protein variant, in which part of amino acids in the amino acid sequence of SEQ ID NO: 6 is modified by a method such as addition, substitution, deletion, etc.

The polynucleotide may be modified by substitution, deletion, insertion, or a combination thereof one or more nucleotides. When the nucleotide sequence is prepared by chemical synthesis, a synthesis method widely known in the art, for example, a method described in a literature (Engels and Uhlmann, Angew Chem IntEd Engl., 37:73-127, 1988) may be used. Triester, phosphite, phosphoramidite and H-phosphate methods, PCR and other autoprimer methods, oligonucleotide synthesis methods on solid supports may be used.

In an embodiment of the present invention, when 4CL derived from *Streptomyces coelicolor* and CCR derived from *Arabidopsis thaliana* are used in combination, superior enzymatic activity was obtained, compared to a combination of 4CL derived from *Arabidopsis thaliana* and CCR derived from *Arabidopsis thaliana* (FIG. 5)

The term "homology", as used herein in relation to the sequence, refers to a degree of matching with a given amino acid sequence or nucleotide sequence, and the homology may be expressed as a percentage. In the present invention, a homology sequence having an activity which is identical or similar to the given amino acid sequence or nucleotide sequence is expressed as "% homology". The homology sequence may be determined by, for example, a standard software, specifically, BLAST 2.0, which calculates the parameters such as score, identity, similarity, etc., or by comparing the sequences in a Southern hybridization experiment under defined stringent conditions, and defining appropriate hybridization conditions are within the skill of the art (Sambrook et al., 1989, infra.), and may be determined by a method well known to those skilled in the art.

The gene may be codon-optimized with respect to the transformant. The codon optimization refers to replacement of codons of the genes by codons of high frequency in a host for efficient expression of the genes in the host. As long as a method for optimization is used to increase protein expression in the transformant, any method known in the art may be used without limitation.

The term "expression cassette", as used herein, refers to a unit cassette capable of expressing cinnamaldehyde, because of including the cinnamaldehyde biosynthesis genes. In the present invention, the expression cassette may be interchangeable with an expression construct. With respect to the objects of the present invention, the expression cassette according to the present invention may be introduced into a strain to produce cinnamaldehyde.

In another aspect, the present invention provides a vector for producing cinnamaldehyde, including the expression cassette.

The term "vector" or "expression vector", as used herein, refers to a DNA construct including a nucleotide sequence of a polynucleotide encoding a target protein, which is operationally linked to a suitable regulatory sequence so that the target protein may be expressed in an appropriate host.

The regulatory sequence includes a promoter to direct transcription, an arbitrary operator sequence to regulate such transcription, a sequence encoding a suitable mRNA ribosome binding site, and a sequence to regulate termination of transcription and translation. The vector, after being transformed into an appropriate host cell, may be replicated or function irrespective of the host genome, or may be integrated into the genome itself.

The vector may include the cinnamaldehyde biosynthesis genes operably linked thereto. The term "operably linked", as used herein, refers to a functional linkage between a nucleotide expression control sequence and a nucleotide sequence encoding a target protein or RNA in such a manner as to allow general functions. For instance, a promoter and a nucleotide sequence encoding a protein or RNA are operably linked to each other to affect expression of a coding sequence. The operable linkage to a recombinant vector may be prepared using a genetic recombinant technique well known in the art, and site-specific DNA cleavage and ligation may be carried out using enzymes that are generally known in the art.

The expression vector used in the present invention is not particularly limited, as long as it may replicate in a host cell, and the expression vector may be any vector known in the art. Example of the vector commonly used may be a natural or recombinant plasmid, cosmid, virus and bacteriophage. For example, as the phage vector or the cosmid vector, pWE15, M13, λMBL3, λMBL4, λIXII, λASHII, λAPII, λt10, λt11, Charon4A, and Charon21A, etc. may be used. As the plasmid vector, pET type, pTrc type, pBR type, pUC type, pBluescriptII type, pGEM type, pTZ type, pCL type, pMAL type, pHT type, etc. may be used. The vector usable in the present invention is not particularly limited, and any known expression vector may be used. Specifically, pET22b, pTrc99a, pDZ, pACYC177, pACYC184, pCL, pECCG117, pUC19, pBR322, pMW118, pCC1BAC, pMAL-p2x, or pHT43 vector, etc. may be used.

The vector of the present invention may be integrated into the chromosome by homologous recombination, and therefore, it may further include a selection marker to ensure the chromosomal insertion.

The appropriate expression vector may include a signal sequence or a leader sequence for targeting membranes or secretion as well as expression regulatory elements, such as a promoter, an operator, an initiation codon, a stop codon, a polyadenylation signal and an enhancer, and may be constructed in various forms depending on the purpose thereof. The initiation and stop codons are generally considered as part of a nucleotide sequence encoding a target protein, and are necessary to be functional in an individual to whom a genetic construct has been administered, and must be in frame with the coding sequence. The promoter of the vector may be constitutive or inducible. Further, the expression vector may include a selection marker that allows the selection of host cells including the vector, and a replicable expression vector may include a replication origin. The vector may be self-replicable, or may be integrated into the host DNA.

Furthermore, the expression vector may further include a protein tag removed by using endopeptidase for easy detection of cinnamaldehyde. The tag refers to a molecule which exhibits a quantifiable activity or characteristic, and examples thereof may include fluorescent molecules including a chemical fluorescence such as fluorescein, and a polypeptide fluorescence such as green fluorescent protein (GFP) and related proteins; and an epitope tag such as a Myc tag, a Flag tag, a histidine tag, a leucine tag, an IgG tag, a streptavidin tag, etc. When the epitope tag is used, a peptide tag consisting of preferably 6 or more amino acid residues, and more preferably 8 to 50 amino acid residues may be used.

A method of preparing the vector is not particularly limited, and any method commonly used in the art may be used.

In still another aspect, the present invention provides a transformant for producing cinnamaldehyde, including the vector.

The "producing", as used herein, is intended to include secretion of cinnamaldehyde out of cells, for example, secretion of cinnamaldehyde into a medium, as well as production of cinnamaldehyde within a strain.

The "transformation", as used herein, refers to introduction of a vector including a polynucleotide encoding a target protein into a host cell in such a way that the protein encoded by the polynucleotide may be expressed in the host cell.

As long as the transformation method is a known method in the art, the method may be used without limitation. As long as the transformation method is able to produce cinnamaldehyde, the method may include, but is not particularly limited to, $CaCl_2$ precipitation, a Hanahan method that is an improved $CaCl_2$ method by using DMSO (dimethyl sulfoxide) as a reducing material, electroporation, calcium phosphate precipitation, protoplast fusion, agitation using silicon carbide fiber, *Agrobacterium*-mediated transformation, PEG-mediated transformation, dextran sulfate, lipofectamine, Land desiccation/inhibition-mediated transformation.

As long as the transformed polynucleotide may be expressed in the host cell, it may be either integrated into or placed in the chromosome of the host cell, or exist extrachromosomally. Further, the polynucleotide includes DNA and RNA encoding the target protein. The polynucleotide may be introduced in any form, as long as it may be introduced into the host cell and expressed therein. For example, the polynucleotide may be introduced into the host cell in the form of an expression cassette, which is a gene construct including all elements required for its autonomous expression.

A microorganism which may be used as the transformant may be a microorganism belonging to *Escherichia* sp., *Shigella* sp., *Citrobacter* sp., *Salmonella* sp., *Enterobacter* sp. *Yersinia* sp., *Klebsiella* sp., *Erwinia* sp., *Corynebacterium* sp., *Brevibacterium* sp., *Lactobacillus* sp., *Selenomanas* sp., *Vibrio* sp., *Pseudomonas* sp., *Streptomyces* sp., *Arcanobacterium* sp., *Alcaligenes* sp, etc., but is not limited thereto. Specifically, the microorganism may be a microorganism belonging to *Escherichia* sp.

In still another aspect, the present invention provides a method of preparing cinnamaldehyde, including culturing the transformant.

In a specific embodiment of the present invention, the transformant having cinnamaldehyde productivity was cultured and then, a production amount of cinnamaldehyde included in a culture was measured. As a result, it was confirmed that cinnamaldehyde may be produced from the microorganism in a yield of 1.98 mg/L (FIGS. 6 to 8).

The term "culturing", as used herein, refers to a method of growing the microorganism under artificially controlled environmental conditions. In the present invention, the method of culturing the transformant may be performed by using any method widely known in the art. Specifically, as long as the culturing may be performed to express and produce cinnamaldehyde of the present invention, it may be performed by, but is not particularly limited to, a known batch culture, continuous culture, fed-batch culture, etc.

In this regard, the culture conditions are not particularly limited, but an optimal pH (e.g., pH 5 to pH 9, preferably pH 6 to pH 8, and most preferably pH 6.8) may be maintained by using a basic chemical (e.g., sodium hydroxide, potassium hydroxide, or ammonia) or an acidic chemical (e.g., phosphoric acid or sulfuric acid). An aerobic condition may be maintained by adding oxygen or oxygen-containing gas mixture to the culture. The culture temperature may be maintained at 20° C. to 45° C., and preferably at 25° C. to 40° C., and the culturing may be preferably performed for about 10 hrs to 160 hrs.

Media used for the culturing need to meet requirements for growth of particular strains in an appropriate manner by controlling temperature, pH. etc. in a common medium containing appropriate carbon sources, nitrogen sources, amino acids, vitamin, etc.

A carbon source to be used may be sugar and carbohydrate (e.g., glucose, sucrose, lactose, fructose, maltose, molasses, starch, and cellulose), oil and fat (e.g., soybean oil, sunflower oil, peanut oil, and coconut oil), a fatty acid (e.g., palmitic acid, stearic acid, and linolenic acid), an alcohol (e.g., glycerol and ethanol), and an organic acid (e.g., acetic acid). The carbon sources may be used alone or in a mixture.

A nitrogen source may be a nitrogen-containing organic compound (e.g., peptone, yeast extract, meat extract, malt extract, corn steep liquor, soy meal, and urea) or an inorganic compound (e.g., ammonium sulfate, ammonium chloride, ammonium phosphate, ammonium carbonate, and ammonium nitrate). The nitrogen source may be used alone or in a mixture.

A phosphorus source may be potassium dihydrogen phosphate, dipotassium hydrogen phosphate, corresponding sodium-containing salts, etc. The phosphorus source may be used alone or in a mixture. The culture medium may include essential growth-promoting materials such as metal salts (e.g., magnesium sulfate or iron sulfate), amino acids, and vitamins.

Further, proper precursors may be added to the culture medium. These materials may be added to the culture during culturing by an appropriate method in a batch, fed-batch, or continuous mode, but are not limited thereto. pH of the culture may be adjusted by a proper method using a basic compound such as sodium hydroxide, potassium hydroxide, or ammonia, or an acidic compound such as phosphoric acid or sulfuric acid.

In the present invention, the medium may be used in the same meaning as the culture medium.

For example, the preparation method may further include collecting cinnamaldehyde from the cultured transformant or a culture thereof.

The term "culture", as used herein, refers to a resulting material obtained by culturing the microorganism, and may include all of the medium, the cultured microorganism, and materials secreted by the cultured microorganism. For example, the culture may include nutrient sources required to culture the strain, for example, inorganic salts, amino acids, vitamins, nucleic acids and/or other general components included in a culture medium (or culture liquid), in addition to carbon sources, nitrogen sources, etc. Further, the culture may include, for example, enzymes produced/secreted by the strain, etc.

Since cinnamaldehyde produced by the culturing may be secreted into the medium or may remain within cells, the culture may include cinnamaldehyde produced by culturing the microorganism.

A method of collecting cinnamaldehyde produced in the culturing of the present invention may be performed to collect cinnamaldehyde from the culture liquid by using an appropriate method known in the art according to the culturing method, for example, batch, continuous or fed-batch culture. Specifically, the collecting method may be, for example, centrifugation, filtration, extraction, spraying, drying, evaporation, precipitation, crystallization, electrophoresis, fractional dissolution (e.g., ammonium sulfate precipitation), chromatography (e.g., ion exchange, affinity, hydrophobic, and size exclusion chromatography), etc.

For example, the preparation method may further include purifying the collected cinnamaldehyde. The purifying may be performed by general chromatography including immunoaffinity chromatography, receptor affinity chromatography, hydrophobic interaction chromatography, lectin affinity chromatography, size exclusion chromatography, cation or anion exchange chromatography, high performance liquid chromatography (HPLC), reverse phase HPLC, etc. Further, the desired protein, which is the fusion protein with a specific tag, label, or chelate moiety, may be purified after being recognized by specific binding partners or drug. The purified protein may be cut as desired part of protein, or it may remain as it is. The desired form of the protein having additional amino acid may be produced from the cutting process by cutting the fusion protein.

For example, the transformant may be cultured in a medium containing phenylalanine. The pal gene included in the transformant utilizes phenylalanine as a substrate. Therefore, when the transformant is cultured in the medium containing phenylalanine, cinnamaldehyde may be produced with a superior efficiency.

For example, the transformant may be cultured in a medium containing casamino acid. In an embodiment of the present invention, when the transformant including cinnamaldehyde biosynthesis genes was cultured in the medium containing casamino acid, a maximum production yield was as high as 1.98 mg/L. In contrast, when the transformant including cinnamaldehyde biosynthesis genes was cultured in a medium containing no casamino acid, a maximum production yield was 1.23 mg/L.

Hereinafter, the present invention will be described in detail with reference to the following Examples. However, these Examples are for illustrative purposes only, and the invention is not intended to be limited by these Examples.

Example 1. Preparation of Strain and Plasmid for Recombinant Gene Expression

First, from *Arabidopsis thaliana* cDNA, pal (phenylalanine ammonia-lyase, SEQ ID NO: 17), 4cl (4-coumarate: CoA ligase, SEQ ID NO: 18), and ccr (cinnamoyl-CoA reductase, SEQ ID NO: 5) genes were obtained by polymerase chain reaction using BHB 22-F and BHB 22-R, BHB 20-F and BHB 20-R, BHB 19-F and BHB 19-R of sequences described in the following Table 1.

Further, from *Streptomyces maritimus* pal gene synthesized by codon optimization, pal gene (SEQ ID NO: 19) was obtained by polymerase chain reaction using BHB 31-F and BHB 31-R of sequences described in the following Table 1. Further, from *Streptomyces coelicolor* genomic DNA, 4cl gene (SEQ ID NO: 3) was obtained by polymerase chain reaction using BHB 21-F and BHB 21-R of sequences described in the following Table 1.

TABLE 1

| | | |
|---|---|---|
| BHB 19-F | GCATCTAGAAACACAAACAAGGAAGGAAGATAAATGCACCACCACCACCACCACCACCACATGCCAGTCGACGTAGCC | SEQ ID NO: 7 |
| BHB 19-R | ATGCGCGGCCGCTTATCAAGACCCGATCTTAATGCCATTTTC | SEQ ID NO: 8 |
| BHB 20-F | GCATCTAGACCGAAATCAAAAGGAACACCAACGTATGCACCACCACCACCACCACCACCACATGGCGCCACAAGAACAAG | SEQ ID NO: 9 |
| BHB 20-R | ATGCGCGGCCGCTTATCACAATCCATTTGCTAGTTTTGCCC | SEQ ID NO: 10 |
| BHB 21-F | GCATCTAGACGAATACCTGGAGGACCTAAACAGTATGCACCACCACCACCACCACCACCACATGTTCCGCAGCGAGTAC | SEQ ID NO: 11 |
| BHB 21-R | ATGCGCGGCCGCTTATCATCGCGGCTCCCTGAGCT | SEQ ID NO: 12 |
| BHB 22-F | GCATCTAGACACCTTAAGGAGGTCTATCTTTCATATGCACCACCACCACCACCACCACCACATGGAGATTAACGGGGCAC | SEQ ID NO: 13 |
| BHB 22-R | ATGCGCGGCCGCTTATCAACATATTGGAATGGGAGCTCC | SEQ ID NO: 14 |
| BHB 31-F | GCATTCTAGACCCAACGAAGGGGGAACCACACAATATGCACCACCACCACCACCACCACCACACCTTCGTTATTGAACTGGATATGAATGTTACCC | SEQ ID NO: 15 |
| BHB 31-R | ATGCGCGGCCGCTTATCAGTGTGCTGCCACGGCTG | SEQ ID NO: 16 |

Respective PCR products were digested with restriction enzymes, XbaI and HindIII, and each of the products was ligated to a vector described in the following Table 2 and FIG. 2

TABLE 2

| Strain | Relevant Characteristics |
|---|---|
| E. coli MG1655 | F⁻ λ⁻ ilvG⁻rfb⁻50rph⁻1 |
| E. coli BL21 (DE3) | F ompT gal dcm lon hsdS$_B$ (r$_B^-$ m$_B^-$) λ (DE3 [lacI lacUV5-T7 gene 1 ind1 sam7 nin5]) |
| E. coli W3110 | F⁻ λ⁻ rph⁻1 INV(rrnD, rrnE) |
| E. coli NST74 | E. coli W3110 derivative (aroF aroG tyrR pheA pheAo) |
| Plasmid | Relevant Characteristics |
| pET22b | Amp$^R$, T7 promoter |
| pTrc99a | Amp$^R$, trc promoter |
| pHB-I01 | pET22b derivative, His$_8$-tagA. thaliana PAL |
| pHB-I02 | pET22b derivative, His$_8$-tagA. thaliana 4CL |
| pHB-I03 | pET22b derivative, His$_8$-tagA. thaliana CCR |
| pHB-I04 | pET22b derivative, His$_8$-tagS. maritimus PAL |
| pHB-I05 | pET22b derivative, His$_8$-tagS. coelicolor 4CL |
| pHB-P01 | pTrc99a derivative, FLAG-tag S. maritimus PAL, His$_8$-tagS. coelicolor 4CL, and His$_8$-tagA. thaliana CCR |

After completion of ligation, pHB-I01, pHB-I02, pHB-I03, pHB-104, or pHB-I05 vector was transformed into BL21(DE3) via E. coli strain MG1655. The pHB-P01 vector was transformed into E. coli strain NST74.

Example 2. Isolation and Purification of PAL, 4CL, and CCR Proteins

Each of E. coli strains, BL21(DE3) and NST74, was inoculated in an LB (Luria-Bertani) medium containing 2% glucose and 100 µg/mL ampicillin. The strains were incubated under conditions of 37° C. and 200 rpm for 12 hrs, and then each 1/100 volume thereof was transferred to a fresh LB medium. Thereafter, each of the strains was incubated under the same conditions, until OD$_{600}$ reached 0.6.

Thereafter, BL21(DE3) strain was adapted under conditions of 25° C. and 200 rpm for 30 min for protein production, and then 1 mM IPTG (isopropyl-R-D-thiogalactopyranoside) was added thereto, followed by further incubation for 6 hrs. Meanwhile, NST74 strain was incubated under conditions of 37° C. and 200 rpm after addition of 1 mM IPTG.

Thereafter, the culture medium was centrifuged under conditions of 4° C. and 6000 rpm for 10 min, and then a supernatant was discarded. A pellet was resuspended in a buffer (50 mM potassium phosphate, 300 mM sodium chloride, pH 7.0), and disrupted using a sonicator to obtain a cell suspension. Thereafter, this cell suspension was centrifuged under conditions of 4° C. and 10000 rpm for 10 min, and a water-soluble supernatant was obtained.

Thereafter, from the cell suspension, PAL, 4CL, and CCR proteins having 8× histidine tag were purified by IMAC (immobilized metal affinity chromatography).

Further, the water-soluble supernatant was filtered using a 0.45 µm filter, and added to Talon® metal affinity resin pretreated with a binding buffer (50 mM potassium phosphate, 300 mM sodium chloride, pH 7.0). Thereafter, the resin was washed with 10 mL of a washing buffer (50 mM potassium phosphate, 300 mM sodium chloride, 15 mM imidazole, pH 7.0), and then final proteins were purified by using 1 mM elution buffer (50 mM potassium phosphate, 300 mM sodium chloride, 150 mM imidazole, pH 7.0).

Experimental Example 1. Quantification of PAL, 4CL, and CCR Proteins

The purified proteins were quantified by densitometry using 12% (w/v) SDS-PAGE (sodium dodecyl sulfate-polyacrylamide gel electrophoresis) and total protein assay using BSA (bovine serum albumin), and the results are shown in FIG. 3.

In FIG. 3, lane M represents the protein size. Lane 1 to lane 3 represent a total protein (total), a soluble protein (soluble), an eluted protein after purification (elution) of Arabidopsis thaliana PAL enzyme, respectively. Lane 4 to lane 6 represent a total protein (total), a soluble protein (soluble), an eluted protein after purification (elution) of Arabidopsis thaliana 4CL enzyme, respectively. Lane 7 to lane 9 represent a total protein (total), a soluble protein (soluble), an eluted protein after purification (elution) of Arabidopsis thaliana CCR enzyme, respectively. Lane 10 to lane 12 represent a total protein (total), a soluble protein (soluble), an eluted protein after purification (elution) of *Streptomyces maritimus* PAL enzyme, respectively. Lane 13 to lane 15 represent a total protein (total), a soluble protein (soluble), an eluted protein after purification (elution) of *Streptomyces coelicolor* 4CL enzyme, respectively.

With regard to the size of each protein, *Arabidopsis thaliana* PAL was 78 kDa (solid arrow), *Arabidopsis thaliana* 4CL was 61 kDa (dashed arrow), *Arabidopsis thaliana* CCR was 37 kDa (closed triangle), *Streptomyces maritimus* PAL was 56 kDa (open triangle), *Streptomyces coelicolor* 4CL was 55 kDa (open triangle), indicating that PAL, 4CL, and CCR proteins were produced well.

Experimental Example 2. Analysis of Enzymatic Activity

Activities of PAL, 4CL, and CCR proteins purified in Example 2 were analyzed by extracellular reaction.

First, to analyze the activity of PAL, 100 mM Tris-HCl, 0.2 mM phenylalanine, and 200 μg/mL of purified PAL enzyme were reacted. To analyze the activities of 4CL and CCR, 400 mM Tris-HCl, 5 mM ATP, 5 mM magnesium chloride, 0.3 mM Coenzyme A, 0.5 mM trans-cinnamate, and each 50 μg/mL of the purified 4CL and CCR enzymes were reacted.

After the reaction was allowed at 30° C. for 1 hr, cinnamate produced by PAL enzyme and cinnamaldehyde produced by 4CL and CCR enzymes were analyzed by reverse-phase high-performance liquid chromatography (reverse-phase HPLC). In detail, in a ZORBAX Eclipse AAA column (150×4.6 mm; 3.5 μm; Agilent, Calif., USA), a mobile phase A was 0.1% trifluoroacetic acid, and a mobile phase B was acetonitrile. A ratio of acetonitrile was gradually increased from 10% for initial 1 min to 70% for 9 min. A temperature of the column was 40° C., and a flow rate was maintained at 1 mL/min.

Standard solutions (1, 10, 50, 100, and 200 mg/L of cinnamate, and 0.41, 4.1, 41, 82, and 136.7 mg/L of cinnamaldehyde) were used to create standard curves, which were used to determine the quantities of the final products, cinnamate (CA in FIG. 4) and cinnamaldehyde (CAD in FIG. 5), respectively.

As shown in FIG. 4, PAL derived from *Streptomyces maritimus* was found to have higher activity than PAL derived from *Arabidopsis thaliana*. Further, as shown in FIG. 5, when a combination of 4CL derived from *Streptomyces maritimus* and CCR derived from *Arabidopsis thaliana* was used, a high enzymatic activity was observed, compared to a combination of 4CL derived from *Arabidopsis thaliana* and CCR derived from *Arabidopsis thaliana*.

Experimental Example 3. High-Cell Density Cultivation

First, 200 mL of pHB-P01-including *E. coli* strain NST74 which was adapted to an R/2 semi-defined medium (6.75 g/L potassium dihydrogen phosphate, 2 g/L ammonium phosphate dibasic, 0.85 g/L citric acid, 0.7 g/L magnesium sulfate heptahydrate, 5 mL/L trace metal solution (TMS; 10 g/L iron sulfate heptahydrate, 2.2 g/L zinc sulfate heptahydrate, 2 g/L calcium chloride dehydrate, 1 g/L copper sulfate pentahydrate, 0.58 g/L manganese sulfate pentahydrate, 0.1 g/L ammonium heptamolybdate tetrahydrate, 0.02 g/L sodium tetraborate decahydrate, pH 6.8) was incubated at 37'C and 200 rpm for 12 hrs.

Thereafter, the strain was inoculated in 1.8 L of the same medium at a total volume of 2 L, and high-density cultivation was performed in a 5 L-bioreactor. When pH was lower than 6.77, 50% (v/v) ammonia was introduced. When pH was higher than 6.86, a feeding solution was introduced. As the feeding solution, a complex feeding solution 1 (500 g/L glucose, 75 g/L yeast extract, 20 g/L magnesium sulfate heptahydrate), a complex feeding solution 2 (500 g/L glucose, 100 g/L casamino acid, 20 g/L magnesium sulfate heptahydrate), a defined feeding solution 1 (700 g/L glucose, 20 g/L magnesium sulfate heptahydrate), or a defined feeding solution 2 (500 g/L glucose, 20 g/L magnesium sulfate heptahydrate, 0.81 g/L phenylalanine) was used.

The temperature was maintained at 37° C., and dissolved oxygen (DO) was maintained at 40% by supplying oxygen, after an agitation rate was increased to 1000 rpm. When optical density ($OD_{600}$) reached 60, 1 mM IPTG was introduced to produce proteins (enzymes). An anti-foaming agent was introduced by manually after sterilization.

The cultured *E. coli* strain was separately collected at an optical density ($OD_{600}$) of 4 at each time point, and used for protein analysis. A supernatant of the culture was filtered using a 0.22 μm filter, and used in quantification of cinnamaldehyde by reverse-phase HPLC.

FIG. 6 shows optical density ($OD_{600}$; open circle) measured at each time point and the concentration of cinnamaldehyde (CAD con.; closed circle), after complex feeding solution 1 was used as the feeding solution. A maximum production yield was 1.23 mg/L.

FIG. 7 shows optical density ($OD_{600}$; open circle) measured at each time point and the concentration of cinnamaldehyde (CAD con.; closed circle), after complex feeding solution 2 was used as the feeding solution. A maximum production yield was 1.98 mg/L.

FIG. 8 shows optical density ($OD_{600}$; open circle) measured at each time point and the concentration of cinnamaldehyde (CAD con.; closed circle), after defined feeding solution 1 was used as the feeding solution. A maximum production yield was 0.71 mg/L.

FIG. 9 shows optical density ($OD_{600}$; open circle) measured at each time point and the concentration of cinnamaldehyde (CAD con.; closed circle), after defined feeding solution 2 was used as the feeding solution. A maximum production yield was 1.05 mg/L.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

Effect of the Invention

An expression cassette for producing cinnamaldehyde according to the present invention, a vector including the same, a transformant including the same, and a method of preparing cinnamaldehyde by using the same may be used to produce cinnamaldehyde with high efficiency.

INDUSTRIAL APPLICABILITY

Accordingly, the present invention provides an expression cassette for producing cinnamaldehyde, a vector including the same, a transformant including the same, and a method of preparing cinnamaldehyde by using the same

What is claimed is:

1. An expression cassette for producing cinnamaldehyde, the expression cassette comprising a pal (phenylalanine ammonia lyase) gene of *Streptomyces maritimus*, a 4cl (4-coumarate:CoA ligase) gene of *Streptomyces coelicolor*, and a ccr (cinnamoyl Co-A reductase) gene of *Arabidopsis thaliana*, wherein
the pal gene encodes a protein having the amino acid sequence of SEQ ID NO: 2;
the 4cl gene encodes a protein having the amino acid sequence of SEQ ID NO: 4; and
the ccr gene encodes a protein having the amino acid sequence of SEQ ID NO: 6.

2. The expression cassette of claim 1, wherein the pal gene has the nucleotide sequence of SEQ ID NO. 1 or SEQ ID NO: 19.

3. The expression cassette of claim 1, wherein the 4cl gene has the nucleotide sequence of SEQ ID NO. 3.

4. The expression cassette of claim 1, wherein the ccr gene has the nucleotide sequence of SEQ ID NO: 5.

5. A vector for producing cinnamaldehyde, the vector comprising the expression cassette of claim 1.

6. A transformed cell comprising the vector of claim 5.

7. The transformed cell of claim 6, wherein the transformed cell is a microorganism belonging to *Escherichia* sp.

8. A method of preparing cinnamaldehyde, the method comprising culturing the transformant of claim 6.

9. The method of preparing cinnamaldehyde of claim 8, wherein the transformant is cultured in a medium comprising phenylalanine.

10. The method of preparing cinnamaldehyde of claim 8, wherein the transformant is cultured in a medium comprising casamino acid.

* * * * *

SEQUENCE LISTING

<160> NUMBER OF SEQ ID NOS: 19

<210> SEQ ID NO 1
<211> LENGTH: 1569
<212> TYPE: DNA
<213> ORGANISM: Streptomyces maritimus

<400> SEQUENCE: 1

| | | | | | |
|---|---|---|---|---|---|
| atgaccttcg | tcatagagct | cgacatgaac | gtcacgctcg | accaacttga | ggacgcggcg | 60 |
| cgacagcgca | cgcccgtgga | gctgtccgca | cccgtccgct | ccgcgtccg | cgcctcgcgc | 120 |
| gacgtgttgg | tgaagttcgt | gcaggacgaa | cgtgtcatct | acggggtcaa | caccagcatg | 180 |
| gggggcttcg | tcgaccacct | cgtcccggtg | tcccaggccc | ggcagctcca | ggagaacctg | 240 |
| atcaacgcgg | tcgccaccaa | cgtggggcg | tatctggacg | acacgaccgc | cggaccatc | 300 |
| atgctgtccc | gcatcgtgtc | gctggcgcgc | gggaactccg | cgatcacccc | ggcgaatctg | 360 |
| gacaagctgg | tggccgtact | caacgccggg | atcgtgccgt | gcatcccgga | gaagggctct | 420 |
| ttgggcacca | gcggtgacct | cggcccgctg | gccgcgatcg | ccctggtgtg | cgcggggcag | 480 |
| tggaaggccc | gctacaacgg | tcagatcatg | cccgggcggc | aggccctgtc | cgaggccggc | 540 |
| gtcgagccga | tggagctgag | ctacaaggat | ggcctggccc | tgatcaacgg | cacgtcaggc | 600 |
| atggtcggcc | tgggcaccat | ggtcctccag | gccgcgcgcc | ggctcgtgga | ccgctacctg | 660 |
| caggtgtccg | cgttgtcggt | cgagggcctg | gcaggcatga | cgaaaccgtt | cgaccctcgc | 720 |
| gtgcacggcg | tcaagccgca | ccgcgggcag | cgtcaggtgg | cctcgcggtt | gtgggagggg | 780 |
| cttgccgact | cgcacctggc | ggtcaacgaa | ctggacaccg | agcagaccct | ggccggagag | 840 |
| atgggcacgg | tcgccaaggc | cggttcgctg | gcgatcgagg | acgcctactc | catccggtgc | 900 |
| acgccgcaga | tcctcggtcc | cgtggtcgat | gtgctggacc | ggatcggggc | gaccctgcag | 960 |
| gacgagctga | actcctccaa | cgacaacccg | atcgtcctgc | cggaggaggc | ggaggtgttc | 1020 |
| cacaacgggc | acttccacgg | ccagtacgtg | gccatggcca | tggaccacct | gaacatggcc | 1080 |
| ctggccaccg | tgaccaatct | cgccaaccgg | cgcgtggacc | gcttcctgga | caagagcaac | 1140 |
| agcaacgggc | tgcccgcctt | cctgtgccgg | gaagatccgg | gactgcgcct | gggcctgatg | 1200 |
| ggcggccagt | tcatgaccgc | gtcgatcacc | gcggagaccc | gcaccctgac | cattccgatg | 1260 |
| tcggtgcagt | ccctcacgag | tacgcggac | ttccaggaca | tcgtgtcctt | cggattcgtc | 1320 |
| gccgcccgcc | gcgcccggga | ggtactcacc | aacgctgcct | acgtggtggc | cttcgagctg | 1380 |
| ctgtgcgcct | gccaggccgt | cgacatccgc | ggcgcggaca | aactgtcctc | cttcacccgc | 1440 |
| ccgctctatg | agcgcacccg | caagatcgtg | ccgttcttcg | accgggacga | gaccatcacc | 1500 |
| gactacgtcg | agaagctggc | ggccgacctg | atcgcgggcg | agcccgtcga | cgctgccgtg | 1560 |
| gcggcgcac | | | | | | 1569 |

<210> SEQ ID NO 2
<211> LENGTH: 523
<212> TYPE: PRT
<213> ORGANISM: Streptomyces maritimus

<400> SEQUENCE: 2

Met Thr Phe Val Ile Glu Leu Asp Met Asn Val Thr Leu Asp Gln Leu
1               5                   10                  15

Glu Asp Ala Ala Arg Gln Arg Thr Pro Val Glu Leu Ser Ala Pro Val

```
                20                  25                  30
Arg Ser Arg Val Arg Ala Ser Arg Asp Val Leu Val Lys Phe Val Gln
            35                  40                  45
Asp Glu Arg Val Ile Tyr Gly Val Asn Thr Ser Met Gly Gly Phe Val
        50                  55                  60
Asp His Leu Val Pro Val Ser Gln Ala Arg Gln Leu Gln Glu Asn Leu
65                  70                  75                  80
Ile Asn Ala Val Ala Thr Asn Val Gly Ala Tyr Leu Asp Asp Thr Thr
                85                  90                  95
Ala Arg Thr Ile Met Leu Ser Arg Ile Val Ser Leu Ala Arg Gly Asn
            100                 105                 110
Ser Ala Ile Thr Pro Ala Asn Leu Asp Lys Leu Val Ala Val Leu Asn
        115                 120                 125
Ala Gly Ile Val Pro Cys Ile Pro Glu Lys Gly Ser Leu Gly Thr Ser
        130                 135                 140
Gly Asp Leu Gly Pro Leu Ala Ala Ile Ala Leu Val Cys Ala Gly Gln
145                 150                 155                 160
Trp Lys Ala Arg Tyr Asn Gly Gln Ile Met Pro Gly Arg Gln Ala Leu
                165                 170                 175
Ser Glu Ala Gly Val Glu Pro Met Glu Leu Ser Tyr Lys Asp Gly Leu
            180                 185                 190
Ala Leu Ile Asn Gly Thr Ser Gly Met Val Gly Leu Gly Thr Met Val
        195                 200                 205
Leu Gln Ala Ala Arg Arg Leu Val Asp Arg Tyr Leu Gln Val Ser Ala
        210                 215                 220
Leu Ser Val Glu Gly Leu Ala Gly Met Thr Lys Pro Phe Asp Pro Arg
225                 230                 235                 240
Val His Gly Val Lys Pro His Arg Gly Gln Arg Gln Val Ala Ser Arg
                245                 250                 255
Leu Trp Glu Gly Leu Ala Asp Ser His Leu Ala Val Asn Glu Leu Asp
            260                 265                 270
Thr Glu Gln Thr Leu Ala Gly Glu Met Gly Thr Val Ala Lys Ala Gly
        275                 280                 285
Ser Leu Ala Ile Glu Asp Ala Tyr Ser Ile Arg Cys Thr Pro Gln Ile
        290                 295                 300
Leu Gly Pro Val Val Asp Val Leu Asp Arg Ile Gly Ala Thr Leu Gln
305                 310                 315                 320
Asp Glu Leu Asn Ser Ser Asn Asp Asn Pro Ile Val Leu Pro Glu Glu
                325                 330                 335
Ala Glu Val Phe His Asn Gly His Phe His Gly Gln Tyr Val Ala Met
            340                 345                 350
Ala Met Asp His Leu Asn Met Ala Leu Ala Thr Val Thr Asn Leu Ala
        355                 360                 365
Asn Arg Arg Val Asp Arg Phe Leu Asp Lys Ser Asn Ser Asn Gly Leu
        370                 375                 380
Pro Ala Phe Leu Cys Arg Glu Asp Pro Gly Leu Arg Leu Gly Leu Met
385                 390                 395                 400
Gly Gly Gln Phe Met Thr Ala Ser Ile Thr Ala Glu Thr Arg Thr Leu
                405                 410                 415
Thr Ile Pro Met Ser Val Gln Ser Leu Thr Ser Thr Ala Asp Phe Gln
            420                 425                 430
Asp Ile Val Ser Phe Gly Phe Val Ala Ala Arg Arg Ala Arg Glu Val
        435                 440                 445
```

Leu Thr Asn Ala Ala Tyr Val Ala Phe Glu Leu Leu Cys Ala Cys
    450                 455                 460

Gln Ala Val Asp Ile Arg Gly Ala Asp Lys Leu Ser Ser Phe Thr Arg
465                 470                 475                 480

Pro Leu Tyr Glu Arg Thr Arg Lys Ile Val Pro Phe Phe Asp Arg Asp
                485                 490                 495

Glu Thr Ile Thr Asp Tyr Val Glu Lys Leu Ala Ala Asp Leu Ile Ala
            500                 505                 510

Gly Glu Pro Val Asp Ala Ala Val Ala Ala His
            515                 520

<210> SEQ ID NO 3
<211> LENGTH: 1566
<212> TYPE: DNA
<213> ORGANISM: Streptomyces coelicolor

<400> SEQUENCE: 3

```
atgttccgca gcgagtacgc agacgtcccg cccgtcgacc tgcccatcca cgacgccgtg      60
ctcggcgggg ccgccgcctt cgggagcacc ccggcgctga tcgacggcac cgacggcacc     120
accctcacct acgagcaggt ggaccggttc accggcgcg tcgccgccgc cctcgccgag     180
accggcgtgc gcaagggcga cgtcctcgcc ctgcacagcc caacaccgt cgccttcccc     240
ctggccttct acgccgccac ccgcgcgggc gcctccgtca ccacggtgca tccgctcgcg     300
acggcggagg agttcgccaa gcagctgaag gacagcgcgg cccgctggat cgtcaccgtc     360
tcaccgctcc tgtccaccgc ccgccgggcc gccgaactcg cgggcggcgt ccaggagatc     420
ctggtctgcg acagcgcgcc cggtcaccgc tccctcgtcg acatgctggc ctcgaccgcg     480
cccgaaccgt ccgtcgccat cgacccggcc gaggacgtcg ccgccctgcc gtactcctcg     540
ggcaccaccg gcacccccaa gggcgtcatg ctcacacacc ggcagatcgc caccaacctc     600
gcccagctcg aaccgtcgat gccgtccgcg cccggcgacc gcgtcctcgc cgtgctgccg     660
ttcttccaca tctacggcct gaccgccctg atgaacgccc cgctccggct cggcgccacc     720
gtcgtggtcc tgccccgctt cgacctggag cagttcctcg ccgccatcca gaaccaccgc     780
atcaccagcc tgtacgtcgc cccgccgatc gtcctggccc tcgccaaaca ccccctggtc     840
gccgactacg acctctcctc gctgaggtac atcgtcagcg ccgccgcccc gctcgacgcg     900
cgtctcgccg ccgcctgctc gcagcggctc ggcctgccgc cgtcggcca ggcctacggc     960
atgaccgaac tgtccccggg cacccacgtc gtcccctgg acgcgatggc cgacgcgccg    1020
cccggcaccg tcggcaggct catcgcgggc accgagatgc gcatcgtctc cctcaccgac    1080
ccgggcacgg acctccccgc cggagagtcc ggggagatcc tcatccgcgg ccccagatc    1140
atgaagggct acctgggccg ccccgacgcc accgccgcca tgatcgacga ggagggctgg    1200
ctgcacaccg gggacgtcgg acacgtcgac gccgacggct ggctgttcgt cgtcgaccgc    1260
gtcaaggaac tgatcaagta caagggcttc caggtggccc ccgccgaact ggaggccac    1320
ctgctcaccc accccggcgt cgccgacgcg gccgtcgtcg gcgcctacga cgacgacggc    1380
aacgaggtac gcacgccctt cgtcgtccgc cagccggccg cacccggcct cggcgagagc    1440
gagatcatga tgtacgtcgc cgaacgcgtc gccccctaca acgcgtccg ccgggtcacc    1500
ttcgtcgacg ccgtcccccg cgccgcctcc ggcaagatcc tccgccgaca gctcagggag    1560
ccgcga                                                               1566
```

```
<210> SEQ ID NO 4
<211> LENGTH: 522
<212> TYPE: PRT
<213> ORGANISM: Streptomyces coelicolor

<400> SEQUENCE: 4
```

| Met | Phe | Arg | Ser | Glu | Tyr | Ala | Asp | Val | Pro | Pro | Val | Asp | Leu | Pro | Ile |
|---|---|---|---|---|---|---|---|---|---|---|---|---|---|---|---|
| 1 | | | | 5 | | | | | 10 | | | | | 15 | |

His Asp Ala Val Leu Gly Gly Ala Ala Ala Phe Gly Ser Thr Pro Ala
            20                  25                  30

Leu Ile Asp Gly Thr Asp Gly Thr Thr Leu Thr Tyr Glu Gln Val Asp
        35                  40                  45

Arg Phe His Arg Arg Val Ala Ala Leu Ala Glu Thr Gly Val Arg
    50                  55                  60

Lys Gly Asp Val Leu Ala Leu His Ser Pro Asn Thr Val Ala Phe Pro
65                  70                  75                  80

Leu Ala Phe Tyr Ala Ala Thr Arg Ala Gly Ala Ser Val Thr Thr Val
                85                  90                  95

His Pro Leu Ala Thr Ala Glu Glu Phe Ala Lys Gln Leu Lys Asp Ser
            100                 105                 110

Ala Ala Arg Trp Ile Val Thr Val Ser Pro Leu Leu Ser Thr Ala Arg
        115                 120                 125

Arg Ala Ala Glu Leu Ala Gly Gly Val Gln Glu Ile Leu Val Cys Asp
    130                 135                 140

Ser Ala Pro Gly His Arg Ser Leu Val Asp Met Leu Ala Ser Thr Ala
145                 150                 155                 160

Pro Glu Pro Ser Val Ala Ile Asp Pro Ala Asp Val Ala Ala Leu
                165                 170                 175

Pro Tyr Ser Ser Gly Thr Thr Gly Thr Pro Lys Gly Val Met Leu Thr
        180                 185                 190

His Arg Gln Ile Ala Thr Asn Leu Ala Gln Leu Glu Pro Ser Met Pro
    195                 200                 205

Ser Ala Pro Gly Asp Arg Val Leu Ala Val Leu Pro Phe Phe His Ile
210                 215                 220

Tyr Gly Leu Thr Ala Leu Met Asn Ala Pro Leu Arg Leu Gly Ala Thr
225                 230                 235                 240

Val Val Val Leu Pro Arg Phe Asp Leu Glu Gln Phe Leu Ala Ala Ile
                245                 250                 255

Gln Asn His Arg Ile Thr Ser Leu Tyr Val Ala Pro Ile Val Leu
        260                 265                 270

Ala Leu Ala Lys His Pro Leu Val Ala Asp Tyr Asp Leu Ser Ser Leu
    275                 280                 285

Arg Tyr Ile Val Ser Ala Ala Ala Pro Leu Asp Ala Arg Leu Ala Ala
290                 295                 300

Ala Cys Ser Gln Arg Leu Gly Leu Pro Val Gly Gln Ala Tyr Gly
305                 310                 315                 320

Met Thr Glu Leu Ser Pro Gly Thr His Val Val Pro Leu Asp Ala Met
                325                 330                 335

Ala Asp Ala Pro Pro Gly Thr Val Gly Arg Leu Ile Ala Gly Thr Glu
        340                 345                 350

Met Arg Ile Val Ser Leu Thr Asp Pro Gly Thr Asp Leu Pro Ala Gly
    355                 360                 365

Glu Ser Gly Glu Ile Leu Ile Arg Gly Pro Gln Ile Met Lys Gly Tyr
370                 375                 380

Leu Gly Arg Pro Asp Ala Thr Ala Ala Met Ile Asp Glu Glu Gly Trp
385                 390                 395                 400

Leu His Thr Gly Asp Val Gly His Val Asp Ala Asp Gly Trp Leu Phe
            405                 410                 415

Val Val Asp Arg Val Lys Glu Leu Ile Lys Tyr Lys Gly Phe Gln Val
        420                 425                 430

Ala Pro Ala Glu Leu Glu Ala His Leu Leu Thr His Pro Gly Val Ala
    435                 440                 445

Asp Ala Val Val Gly Ala Tyr Asp Asp Asp Gly Asn Glu Val Pro
    450                 455                 460

His Ala Phe Val Val Arg Gln Pro Ala Ala Pro Gly Leu Ala Glu Ser
465                 470                 475                 480

Glu Ile Met Met Tyr Val Ala Glu Arg Val Ala Pro Tyr Lys Arg Val
                485                 490                 495

Arg Arg Val Thr Phe Val Asp Ala Val Pro Arg Ala Ala Ser Gly Lys
            500                 505                 510

Ile Leu Arg Arg Gln Leu Arg Glu Pro Arg
        515                 520

<210> SEQ ID NO 5
<211> LENGTH: 1032
<212> TYPE: DNA
<213> ORGANISM: Arabidopsis thaliana

<400> SEQUENCE: 5
atgccagtcg acgtagcctc accggccgga aaaaccgtct gcgtcaccgg agctggtgga      60
tacatcgctt cttggattgt aagatactt ctcgagagag gttacacagt caaaggaacc     120
gtacggaatc cagatgatcc gaagaacaca catttgagag aactagaagg aggaaaggag     180
agactgattc tgtgcaaagc agatcttcag gactacgagg ctcttaaggc ggcgattgat     240
ggttgcgacg gcgtctttca cacggcttct cctgtcaccg acgatccgga acaaatggtg     300
gagccggccg tgaatggagc caagtttgta attaatgctg cggctgaggc caaggtcaag     360
cgcgtggtca tcacctcctc cattggtgcc gtctacatgg acccgaaccg tgaccctgag     420
gctgtcgttg acgaaagttg ttggagtgat cttgacttct gcaaaaacac caagaattgg     480
tattgttacg gcaagatggt ggcggaacaa gcggcgtggg agacagcaaa ggagaaaggt     540
gttgacttgg tggtgttgaa tccggtgctg gttcttggac cgccgttaca gccgacgatc     600
aacgccagtc tttaccacgt cctcaaatat ctaaccggct cggctaagac ttatgctaat     660
ttgactcaag cttatgtgga tgttcgcgat gtcgcgctgg ctcatgttct ggtctatgag     720
gcaccctcgg cctccggacg ttatctccta gccgagagtg ctcgccaccg cggggaagtt     780
gttgagattc tggctaagct attcccggag tatcctcttc cgaccaagtg caaggacgag     840
aagaacccta gagccaagcc atacaaattc actaaccaga gattaaggga cttaggctta     900
gagttcactt ccaccaagca aagcctctac gacacagtca agagcttaca agagaaaggc     960
catcttgctc ctcctcctcc tcctccttca gcatcgcaag aatccgtgga aaatggcatt    1020
aagatcgggt ct                                                        1032

<210> SEQ ID NO 6
<211> LENGTH: 344
<212> TYPE: PRT
<213> ORGANISM: Arabidopsis thaliana

<400> SEQUENCE: 6

```
Met Pro Val Asp Val Ala Ser Pro Ala Gly Lys Thr Val Cys Val Thr
1               5                   10                  15
Gly Ala Gly Gly Tyr Ile Ala Ser Trp Ile Val Lys Ile Leu Leu Glu
                20                  25                  30
Arg Gly Tyr Thr Val Lys Gly Thr Val Arg Asn Pro Asp Asp Pro Lys
            35                  40                  45
Asn Thr His Leu Arg Glu Leu Glu Gly Gly Lys Glu Arg Leu Ile Leu
50                  55                  60
Cys Lys Ala Asp Leu Gln Asp Tyr Glu Ala Leu Lys Ala Ala Ile Asp
65                  70                  75                  80
Gly Cys Asp Gly Val Phe His Thr Ala Ser Pro Val Thr Asp Asp Pro
                85                  90                  95
Glu Gln Met Val Glu Pro Ala Val Asn Gly Ala Lys Phe Val Ile Asn
                100                 105                 110
Ala Ala Ala Glu Ala Lys Val Lys Arg Val Val Ile Thr Ser Ser Ile
            115                 120                 125
Gly Ala Val Tyr Met Asp Pro Asn Arg Asp Pro Glu Ala Val Val Asp
130                 135                 140
Glu Ser Cys Trp Ser Asp Leu Asp Phe Cys Lys Asn Thr Lys Asn Trp
145                 150                 155                 160
Tyr Cys Tyr Gly Lys Met Val Ala Glu Gln Ala Ala Trp Glu Thr Ala
                165                 170                 175
Lys Glu Lys Gly Val Asp Leu Val Val Leu Asn Pro Val Leu Val Leu
            180                 185                 190
Gly Pro Pro Leu Gln Pro Thr Ile Asn Ala Ser Leu Tyr His Val Leu
        195                 200                 205
Lys Tyr Leu Thr Gly Ser Ala Lys Thr Tyr Ala Asn Leu Thr Gln Ala
210                 215                 220
Tyr Val Asp Val Arg Asp Val Ala Leu Ala His Val Leu Val Tyr Glu
225                 230                 235                 240
Ala Pro Ser Ala Ser Gly Arg Tyr Leu Leu Ala Glu Ser Ala Arg His
                245                 250                 255
Arg Gly Glu Val Val Glu Ile Leu Ala Lys Leu Phe Pro Glu Tyr Pro
            260                 265                 270
Leu Pro Thr Lys Cys Lys Asp Glu Lys Asn Pro Arg Ala Lys Pro Tyr
        275                 280                 285
Lys Phe Thr Asn Gln Lys Ile Lys Asp Leu Gly Leu Glu Phe Thr Ser
290                 295                 300
Thr Lys Gln Ser Leu Tyr Asp Thr Val Lys Ser Leu Gln Glu Lys Gly
305                 310                 315                 320
His Leu Ala Pro Pro Pro Pro Pro Ser Ala Ser Gln Glu Ser Val
                325                 330                 335
Glu Asn Gly Ile Lys Ile Gly Ser
            340

<210> SEQ ID NO 7
<211> LENGTH: 78
<212> TYPE: DNA
<213> ORGANISM: Artificial Sequence
<220> FEATURE:
<223> OTHER INFORMATION: Synthetic primer

<400> SEQUENCE: 7
gcatctagaa acacaaacaa ggaaggaaga taaatgcacc accaccacca ccaccaccac    60
atgccagtcg acgtagcc                                                  78
```

<210> SEQ ID NO 8
<211> LENGTH: 42
<212> TYPE: DNA
<213> ORGANISM: Artificial sequence
<220> FEATURE:
<223> OTHER INFORMATION: Synthetic primer

<400> SEQUENCE: 8
atgcgcggcc gcttatcaag acccgatctt aatgccattt tc                            42

<210> SEQ ID NO 9
<211> LENGTH: 80
<212> TYPE: DNA
<213> ORGANISM: Artificial sequence
<220> FEATURE:
<223> OTHER INFORMATION: Synthetic primer

<400> SEQUENCE: 9
gcatctagac cgaaatcaaa aggaacacca acgtatgcac caccaccacc accaccacca         60
catggcgcca caagaacaag                                                     80

<210> SEQ ID NO 10
<211> LENGTH: 41
<212> TYPE: DNA
<213> ORGANISM: Artificial Sequence
<220> FEATURE:
<223> OTHER INFORMATION: Synthetic primer

<400> SEQUENCE: 10
atgcgcggcc gcttatcaca atccatttgc tagttttgcc c                             41

<210> SEQ ID NO 11
<211> LENGTH: 41
<212> TYPE: DNA
<213> ORGANISM: Artificial Sequence
<220> FEATURE:
<223> OTHER INFORMATION: Synthetic primer

<400> SEQUENCE: 11
atgcgcggcc gcttatcaca atccatttgc tagttttgcc c                             41

<210> SEQ ID NO 12
<211> LENGTH: 35
<212> TYPE: DNA
<213> ORGANISM: Artificial Sequence
<220> FEATURE:
<223> OTHER INFORMATION: Synthetic primer

<400> SEQUENCE: 12
atgcgcggcc gcttatcatc gcggctccct gagct                                    35

<210> SEQ ID NO 13
<211> LENGTH: 80
<212> TYPE: DNA
<213> ORGANISM: Artificial Sequence
<220> FEATURE:
<223> OTHER INFORMATION: Synthetic primer

<400> SEQUENCE: 13
gcatctagac accttaagga ggtctatctt tcatatgcac caccaccacc accaccacca         60
catggagatt aacggggcac                                                     80

<210> SEQ ID NO 14

```
<211> LENGTH: 39
<212> TYPE: DNA
<213> ORGANISM: Artificial Sequence
<220> FEATURE:
<223> OTHER INFORMATION: Synthetic primer

<400> SEQUENCE: 14
atgcgcggcc gcttatcaac atattggaat gggagctcc                              39

<210> SEQ ID NO 15
<211> LENGTH: 96
<212> TYPE: DNA
<213> ORGANISM: Artificial Sequence
<220> FEATURE:
<223> OTHER INFORMATION: Synthetic primer

<400> SEQUENCE: 15
gcattctaga cccaacgaag ggggaaccac acaatatgca ccaccaccac caccaccacc       60
acaccttcgt tattgaactg gatatgaatg ttaccc                                 96

<210> SEQ ID NO 16
<211> LENGTH: 35
<212> TYPE: DNA
<213> ORGANISM: Artificial Sequence
<220> FEATURE:
<223> OTHER INFORMATION: Synthetic primer

<400> SEQUENCE: 16
atgcgcggcc gcttatcagt gtgctgccac ggctg                                  35

<210> SEQ ID NO 17
<211> LENGTH: 2175
<212> TYPE: DNA
<213> ORGANISM: Arabidopsis thaliana

<400> SEQUENCE: 17
atggagatta cggggcaca caagagcaac ggaggaggag tggacgctat gttatgcggc        60
ggagacatca agacaaagaa catggtgatc aacgcggagg atcctctcaa ctggggagct       120
gcagcggagc aaatgaaagg tagccatttg atgaagtga agagaatggt tgctgagttt       180
aggaagccag ttgtgaatct tggtggtgag actctgacca ttggacaagt ggctgcgatc       240
tcaactattg gtaacagtgt gaaggtggag ctatcggaga cagctagagc cggtgtgaat       300
gctagtagtg attgggttat ggagagtatg aacaaaggca ctgatagtta tggtgttact       360
actggttttg gtgctacttc tcatcggaga accaaaaacg gtgtcgcact tcagaaggaa       420
cttattagat tccttaacgc cggaatattc ggaagcacga agaaacaag ccacacattg        480 ccacactccg ccacaagagc cgccatgctt gtacgaatca cactctcct caaggatttt       540 tccggtatcc gatttgagat tctcgaagca attaccagtt tcctcaacaa caacatcact       600
ccatctctcc cctcgtgg tacaatcacc gcctccggag atctcgttcc tctctcctac       660
atcgccggac ttctcaccgg tcgtcccaat tccaaagcta ctggtcccaa cggtgaagct       720
ttaacagcag aggaagcttt caaattagca ggaatcagct ccggattctt tgatctccag       780
cctaaggaag gtctcgcgct agtcaatggc acgcggttg gatctggaat ggcgtcaatg       840
gtgttattcg aaacgaatgt tctctctgtt ttggctgaga ttttgtcggc ggttttcgca       900
gaggtgatga gtggtaagcc tgagttcacc gatcatctca ctcacagact taaacatcat      960
cccggtcaaa tcgaagcggc ggcgataatg gagcatatcc tcgacggaag ctcgtacatg      1020
aaattagctc agaagcttca cgagatggat ccgttacaga aacctaaaca agatcgttac      1080
```

```
gctcttcgta cttctcctca atggttaggt cctcaaatcg aagtgatccg ttacgcaacg   1140
aaatcgatcg agcgtgagat taactccgtc aacgataatc cgttgatcga tgtttcgagg   1200
aacaaggcga ttcacggtgg taacttccaa ggaacaccaa tcggagtttc aatggataac   1260
acgagattgg cgatagcagc gattggtaaa ctcatgtttg ctcaattctc agagcttgtg   1320
aatgatttct acaacaatgg tttaccctcg aatctaaccg cttcgaggaa tccaagtttg   1380
gattatggat tcaagggagc tgagattgca atggcttctt attgttcaga gcttcaatac   1440
ttagctaatc ctgtgactag ccatgttcaa tcagcagagc aacataacca agatgtcaac   1500
tctttgggac taatctcgtc tcgcaaaact tctgaagctg ttgatattct caagcttatg   1560
tcaacaacgt tcctcgttgc gatttgtcaa gctgtggatt tgagacattt ggaggagaat   1620
ttgagacaga ctgtgaagaa cactgtctct caagtggcga agaaagttct tactactgga   1680
gtcaatggtg agcttcatcc ttctcgcttc tgcgaaaagg atttactcaa agttgtagac   1740
cgtgaacaag tctacacata cgcggatgat ccttgtagcg caacgtaccc gttgattcag   1800
aagctgagac aagttattgt tgaccatgct ttgatcaatg gtgagagtga agaatgca    1860 gtgacttcaa tcttccataa gattggagct ttcgaggagg agcttaaggc agtgctaccg   1920
aaagaagtgg aagcagcaag agcagcctac gataacggaa catcggctat cccgaacagg   1980
atcaaggaat gtaggtcgta tccattgtat agattcgtga gggaagagct tggaacagag   2040
cttttgaccg gagagaaagt gacgtcgcct ggagaagagt tcgacaaggt tttcacggcg   2100
atttgtgaag gtaaaatcat tgatccgatg atggaatgtc tcaacgagtg gaacggagct   2160
cccattccaa tatgt                                                   2175

<210> SEQ ID NO 18
<211> LENGTH: 1683
<212> TYPE: DNA
<213> ORGANISM: Arabidopsis thaliana

<400> SEQUENCE: 18
atggcgccac aagaacaagc agtttctcag gtgatggaga acagagcaa caacaacaac     60 agtgacgtca ttttccgatc aaagttaccg gatatttaca tcccgaacca cctatctctc    120
cacgactaca tcttccaaaa catctccgag ttcgccacta agccttgcct aatcaacgga    180
ccaaccggcc acgtgtacac ttactccgac gtccacgtca tctcccgcca aatcgccgcc    240
aattttcaca aactcggcgt taaccaaaac gacgtcgtca tgctcctcct cccaaactgt    300
cccgagttcg tcctctcttt cctcgccgcc tccttccgcg cgcaaccgc caccgccgca    360 aacccttct tcactccggc ggagatagct aaacaagcca agcctccaa caccaaactc     420 ataatcaccg aagctcgtta cgtcgacaaa atcaaaccac ttcaaaacga cgacggagta    480
gtcatcgtct gcatcgacga caacgaatcc gtgccaatcc tgaaggctg cctccgcttc    540 accgagttga ctcagtcgac aaccgaggca tcagaagtca tcgactcggt ggagatttca    600
ccggacgacg tggtggcact acctactcc tctggcacga cgggattacc aaaaggagtg     660
atgctgactc acaagggtct agtcacgagc gttgctcagc aagtcgacgg cgagaacccg    720
aatctttatt tccacagcga tgacgtcata ctctgtgttt tgcccatgtt tcatatctac    780
gctttgaact cgatcatgtt gtgtggtctt agagttggtg cggcgattct gataatgccg    840
aagtttgaga tcaatctgct attggagctg atccagaggt gtaaagtgac ggtggctccg    900
atggttccgc cgattgtgtt ggccattgcg aagtcttcgg agacggagaa gtatgatttg    960
```

| | |
|---|---|
| agctcgataa gagtggtgaa atctggtgct gctcctcttg gtaaagaact tgaagatgcc | 1020 |
| gttaatgcca agtttcctaa tgccaaactc ggtcagggat acggaatgac ggaagcaggt | 1080 |
| ccagtgctag caatgtcgtt aggttttgca aaggaacctt ttccggttaa gtcaggagct | 1140 |
| tgtggtactt ttgtaagaaa tgctgagatg aaaatagttg atccagacac cggagattct | 1200 |
| ctttcgagga atcaacccgg tgagatttgt attcgtggtc accagatcat gaaaggttac | 1260 |
| ctcaacaatc cggcagctac agcagagacc attgataaag acggttggct tcatactgga | 1320 |
| gatattggat tgatcgatga cgatgacgag cttttcatcg ttgatcgatt gaaagaactt | 1380 |
| atcaagtata aaggttttca ggtagctccg gctgagctag aggctttgct catcggtcat | 1440 |
| cctgacatta ctgatgttgc tgttgtcgca atgaaagaag aagcagctgg tgaagttcct | 1500 |
| gttgcatttg tggtgaaatc gaaggattcg gagttatcag aagatgatgt gaagcaattc | 1560 |
| gtgtcgaaac aggttgtgtt ttacaagaga atcaacaaag tgttcttcac tgaatccatt | 1620 |
| cctaaagctc catcagggaa gatattgagg aaagatctga gggcaaaact agcaaatgga | 1680 |
| ttg | 1683 |

<210> SEQ ID NO 19
<211> LENGTH: 1569
<212> TYPE: DNA
<213> ORGANISM: Artificial Sequence
<220> FEATURE:
<223> OTHER INFORMATION: Synthetic phenylalanine ammonia lyase

<400> SEQUENCE: 19

| | |
|---|---|
| atgaccttcg ttattgaact ggatatgaat gttaccctgg accaactgga agatgcggcc | 60 |
| cgtcagcgta ccccggtgga actgtctgcc ccggtgcgtt cccgcgtgcg tgcctcacgt | 120 |
| gatgttctgg tcaaatttgt tcaggacgaa cgcgtgatct atggcgttaa cacctcgatg | 180 |
| ggcggttttcg tggatcatct ggtgccggtt tcacaagcgc gtcagctgca agaaaacctg | 240 |
| attaatgcgg cggcaacgaa tgtgggtgcc tacctggatg acaccacggc acgcaccatt | 300 |
| atgctgtcgc gtatcgttag cctggcgcgc ggcaacagcg ctatcacgcc ggcgaatctg | 360 |
| gataaactgg tcgccgtgct gaacgcaggt attgtgccgt gcatcccgga aaaaggctct | 420 |
| ctgggcacca gcggcgacct gggtccgctg gctgcgatcg ctctggtttg tgcgggccag | 480 |
| tggaaagccc gttataacgg ccagattatg ccgggtcgcc aagccctgtc gaagcaggc | 540 |
| gtggaaccga tggaactgtc atacaaagat ggtctggcgc tgattaatgg cacgagcggt | 600 |
| atggtgggtc tgggcacgat ggtgctgcaa gcagcacgtc gcctggttga tcgctatctg | 660 |
| caagtcagcg ctctgtctgt ggaaggcctg gcgggtatga ccaaaccgtt tgacccgcgt | 720 |
| gttcatggcg tcaaaccgca ccgcggtcag cgtcaagttg cctctcgcct gtgggaaggc | 780 |
| ctggctgata gtcacctggc ggtcaacgaa ctggacacgg aacagaccct ggcaggcgaa | 840 |
| atgggcaccg tggctaaagc gggttcgctg gctattgaag atgcgtatag catccgttgc | 900 |
| acgccgcaga ttctgggtcc ggtggttgat gttctggacc gcatcggtgc aaccctgcaa | 960 |
| gatgaactga atagctctaa cgacaatccg attgtcctgc cggaagaagc ggaagtgttt | 1020 |
| cataacggcc atttccacgg tcaatacgtg gcgatggcga tggatcacct gaatatggct | 1080 |
| ctggcgaccg ttacgaacct ggctaatcgt cgcgtcgatc gttttctgga caaatcaaac | 1140 |
| tcgaatggtc tgccggcctt cctgtgtcgt gaagatccgg gtctgcgtct gggtctgatg | 1200 |
| ggcggtcaat ttatgacggc ctctatcacc gcagaaaccc gtacgctgac cattccgatg | 1260 |
| agtgtgcagt ccctgacgtc aaccgcggat ttccaagaca tcgttagttt tggtttcgtc | 1320 |

```
gctgcacgtc gcgcccgcga agtcctgacc aatgccgcat acgtcgtggc atttgaactg   1380
ctgtgcgcct gtcaggcagt tgatattcgt ggtgcggaca aactgagttc cttcacgcgc   1440
ccgctgtatg aacgcacccg taaaatcgtc ccgtttttcg atcgcgacga aacgattacc   1500
gattacgtgg aaaaactggc agccgacctg attgcgggtg aaccggtgga tgcagccgtg   1560
gcagcacac                                                           1569
```